(12) United States Patent
Tsugawa et al.

(10) Patent No.: US 8,216,970 B2
(45) Date of Patent: Jul. 10, 2012

(54) 1,1-BIS(4-HYDROXYPHENYL)-1-PHENYL ETHANE AND THERMAL RECORDING MATERIAL FOR RECORDING THE SAME

(75) Inventors: Hiroaki Tsugawa, Tokyo (JP); Soichi Uehori, Tokyo (JP); Mituo Yoshifuji, Tokyo (JP)

(73) Assignee: Nipponkayaku Kabushikikaisha, Tokyo (JP)

( * ) Notice: Subject to any disclaimer, the term of this patent is extended or adjusted under 35 U.S.C. 154(b) by 607 days.

(21) Appl. No.: 12/374,329

(22) PCT Filed: Jul. 18, 2007

(86) PCT No.: PCT/JP2007/064203
§ 371 (c)(1),
(2), (4) Date: Jan. 19, 2009

(87) PCT Pub. No.: WO2008/010526
PCT Pub. Date: Jan. 24, 2008

(65) Prior Publication Data
US 2009/0186760 A1   Jul. 23, 2009

(30) Foreign Application Priority Data

Jul. 19, 2006  (JP) .................. 2006-196891

(51) Int. Cl.
*B41M 5/333* (2006.01)
*C07C 39/16* (2006.01)
*C09D 11/00* (2006.01)

(52) U.S. Cl. .................. 503/216; 106/31.18; 428/402; 568/723

(58) Field of Classification Search .................. None
See application file for complete search history.

(56) References Cited

FOREIGN PATENT DOCUMENTS

| | | |
|---|---|---|
| CN | 1557797 A | 12/2004 |
| JP | 60247592 | 12/1985 |
| JP | 62178534 | 1/1986 |
| JP | 200252842 | 2/2002 |

OTHER PUBLICATIONS

Societa Italiana Resine S.p.A., "Bisphenol particularly useful as an intermediate for synthetic resins," Chemical Abstracts, 1966, vol. 65, 3795c, Patent IT 685536.
Societa Italiana Resine S.p.A., "Bisphenol particularly useful as an intermediate for synthetic resins," Chemical Abstracts, 1966, vol. 65, 3795c, Patent IT 685536.—ENLARGED.
International Search Report, PCT/JP2007/064203, Aug 21, 2007.
Office Action from Chinese Patent Office, Counterpart Application No. 200780032624.X, dated Oct. 26, 2011, 3 pp.
Translation of Office Action from Chinese Patent Office, Counterpart Application No. 200780032624.X, dated Oct. 26, 2011, 3 pp.

*Primary Examiner* — Bruce H Hess
(74) *Attorney, Agent, or Firm* — David J. Aston; Peters Verny, LLP

(57) ABSTRACT

This invention provides 1,1-bis(4-hydroxyphenyl)-1-phenylethane having a crystal form characterized by an X-ray diffraction pattern having one sharp and strong peak at 16.4° and three sharp peaks of intermediate intensity at each of 13°-16° and 17°-20.8° and at least three peaks of intermediate intensity at 22°-23° as a diffraction angle (2θ) in an X-ray diffractometry with Cu—K α-rays, and being capable of giving the storing stability of a colored image and a non-colored portion against heat, water or the like and the low-energy color-developing property suitable for high-speed color development.

5 Claims, 2 Drawing Sheets

1,1-BIS(4-HYDROXYPHENYL)-1-PHENYL ETHANE AND THERMAL RECORDING MATERIAL FOR RECORDING THE SAME

TECHNICAL FIELD

This invention relates to 1,1-bis(4-hydroxyphenyl)-1-phenylethane and a heat-sensitive recording material using the same. More particularly, it relates to 1,1-bis(4-hydroxyphenyl)-1-phenylethane having a crystal form characterized by a specified X-ray diffraction pattern in an X-ray diffractometry with Cu—K α-rays.

Heretofore, the heat-sensitive recording material has been typically formed by individually dispersing leuco dyestuff (color-forming compound) and a color-developing compound such as phenolic substance or the like in form of fine particles and mixing them and adding with additives such as a bonding agent, a sensitizer, a filler, a lubricant and the like to form a coating solution and then applying to a paper, a film, a synthetic paper or the like, wherein a color-forming record is obtained by a chemical reaction between the leuco dyestuff and the color-developing compound fused and contacted under heating. In order to develop color on a heat-sensitive recording sheet using such a material are used a thermal printer embedded with a thermal head and the like. This heat-sensitive recording process is widely used in a field of facsimiles, a field of printers for output of a computer, a calculator or the like, a field of recorders for medical measurement, a filed of automatic ticket machines, a filed of heat-sensitive type labels and so on owing to features that (1) noises are not generated in the recording, (2) development, fixation and the like are not required, (3) it is maintenance-free, and (4) machine is relatively cheap as compared with the other recording processes.

Along with the popularization of POS systems in recent retail stores, convenience stores, supermarkets and so on, as a quality of the heat-sensitive recording material are demanded high-speed, low-energy recording seen in a sheet for a cash register or the like as a recording property and a mode like a plain paper that the recorded image but also food labels and so on do not easily develop colors due to contact heat or the like under everyday environment including the heating or thawing treatment in microwave ovens as a storing stability.

As a countermeasure solving these problems are usually proposed a method using a specific heat-fusible compound (JP-A-2002-52842), a method wherein a middle layer (heat insulating effect) is disposed between a substrate and a heat-sensitive recording layer, and a method using a specific color-developing compound (JP-A-S60-247592 and JP-A-2002-52842). Among them, 1,1-bis(4-hydroxyphenyl)-1-phenylethane proposed in JP-A-S60-247592 is high in the convenience as a raw material for a heat-sensitive color-developing layer itself in a point that fogging is not caused in a hygrothermal environment. However, when this compound is used as a color-developing compound, there is a drawback that a low-energy color-developing property adaptable in recently required high-speed coloring is insufficient.

DISCLOSURE OF THE INVENTION

It is, therefore, an object of the invention to solve the drawbacks of the conventional techniques and to provide 1,1-bis(4-hydroxyphenyl)-1-phenylethane capable of giving a storing stability against heat, water or the like and a low-energy color-developing property. Also, it is another object of the invention to provide a heat-sensitive recording material using 1,1-bis(4-hydroxyphenyl)-1-phenylethane and being excellent in the storing stability of a colored image and a non-colored portion against heat, water or the like and excellent in the low-energy color-developing property suitable for high-speed color development.

The inventors have made various studies on a relationship between color-developing property and storing stability of a heat-sensitive recording material using 1,1-bis(4-hydroxyphenyl)-1-phenylethane and observed a case that different behavior may be indicated.

For this end, the inventors have examined reasons indicating the above behavior in detail and found that two crystal forms are existent in 1,1-bis(4-hydroxyphenyl)-1-phenylethane and the two crystal forms indicate entirely-different behaviors as a heat-sensitive recording material.

That is, it has been found that when 1,1-bis(4-hydroxyphenyl)-1-phenylethane is used in the heat-sensitive recording material as a color-developing compound, there are existent two kinds of a crystal being excellent in the storing stability of a matrix portion and a non-colored portion but being poor in the color density in a low-energy color development (hereinafter referred to as α-type crystal) and a crystal being excellent in the low-energy color-developing property suitable for high-speed color development while maintaining properties of the matrix portion and the non-colored portion (hereinafter referred to as β-type crystal).

Thus, it has been found out that the above problems can be solved by using the β-type crystal of 1,1-bis(4-hydroxyphenyl)-1-phenylethane as a color-developing compound in the heat-sensitive recording material, and as a result, the invention has been accomplished.

That is, the summary and construction of the invention are as follows.

1. 1,1-bis(4-hydroxyphenyl)-1-phenylethane having a crystal form characterized by an X-ray diffraction pattern having one sharp and strong peak at 16.4° and three sharp peaks of intermediate intensity at each of 13°-16° and 17°-20.8° and at least three peaks of intermediate intensity at 22°-23° as a diffraction angle (2θ) in an X-ray diffractometry with Cu—K α-rays.

2. A heat-sensitive recording material comprising a substrate and a heat-sensitive color-forming layer formed thereon, which contains a typically achromic to hypochromnic color-forming compound and a color-developing compound capable of coloring the color-forming compound under heating, characterized in that 1,1-bis(4-hydroxyphenyl)-1-phenylethane as described in the item 1 is included as the color-developing compound.

According to the invention, there can be provided 1,1-bis(4-hydroxyphenyl)-1-phenylethane capable of giving a storing stability against heat, water or the like and a low-energy color-developing property. Also, there can be provided a heat-sensitive recording material using such a 1,1-bis(4-hydroxyphenyl)-1-phenylethane and being excellent in the storing stability of a colored image and a non-colored portion against heat, water or the like and excellent in the low-energy color-developing property suitable for high-speed color development.

BRIEF DESCRIPTION OF THE DRAWINGS

In FIGS. 1-3, X-axis shows a diffraction angle (2 Theat(θ) (°)) and Y-axis shows Intensity (cps).

BEST MODE FOR CARRYING OUT THE INVENTION

The invention will be described in detail below. 1,1-bis(4-hydroxyphenyl)-1-phenylethane is a well-known color-developing compound and may be easily available, for example, as a trade name of BisP-AP made by Honshu Chemical Industry Co., Ltd. As mentioned later, the above commercially available one is revealed to be a crystal form of an α-type crystal.

1,1-bis(4-hydroxyphenyl)-1-phenylethane according to the invention has a crystal form of a β-type crystal. At this moment, the β-type crystal of 1,1-bis(4-hydroxyphenyl)-1-phenylethane is obtained by completely dissolving the above α-type crystal of 1,1-bis(4-hydroxyphenyl)-1-phenylethane in ethanol of 1-10 times, preferably 1-5 times as a weight ratio (which may be warmed, if necessary) and adding water of 1-5 times as a weight ratio to the resulting solution dropwise with stirring to precipitate crystals and then filtering the precipitated crystals. That is, the crystal form may be converted into the β-type crystal by crystallizing the α-type crystal of 1,1-bis(4-hydroxyphenyl)-1-phenylethane in an ethanol-water system.

Next, the α-type crystal and β-type crystal of 1,1-bis(4-hydroxyphenyl)-1-phenylethane will be described in detail with reference to the drawings.

Figure 1:
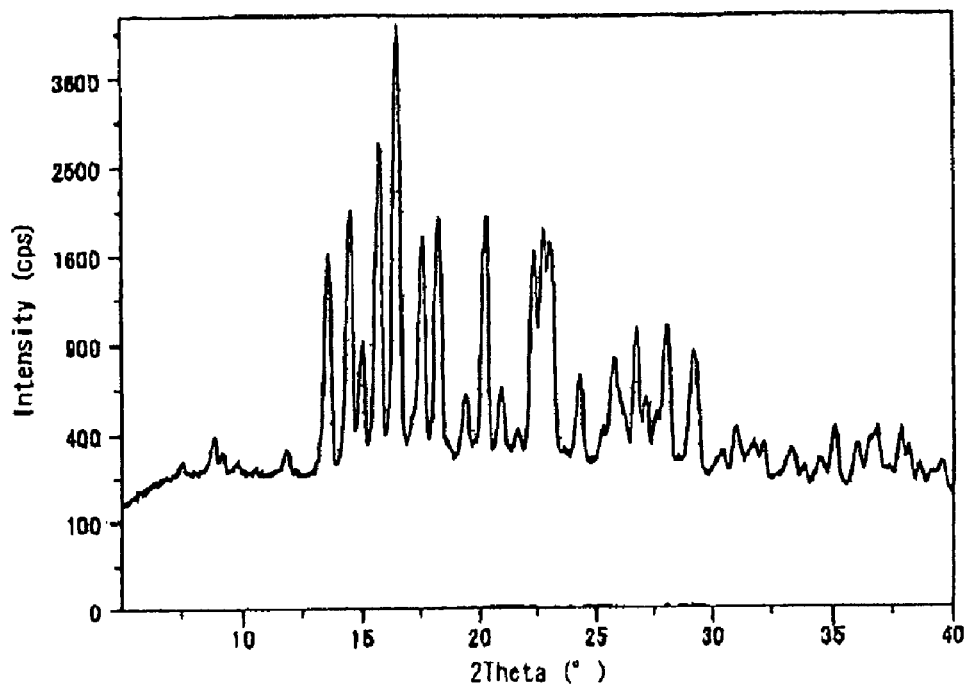
FIG. 1 is an X-ray diffraction pattern with Cu—K α-rays of a β-type crystal of 1,1-bis(4-hydroxyphenyl)-1-phenylethane according to the invention.
Figure 2:
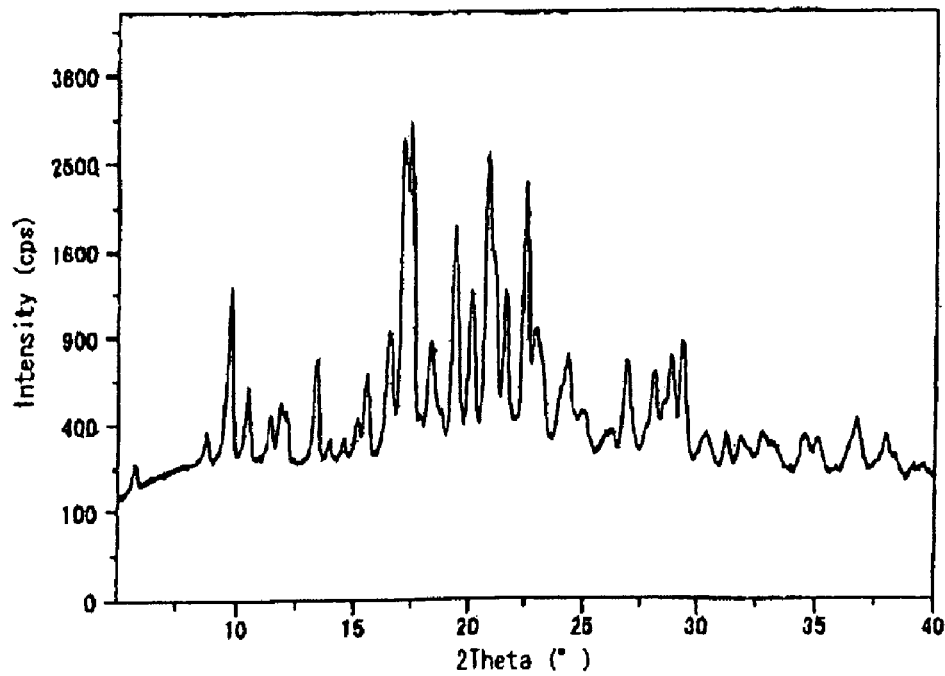
FIG. 2 is an X-ray diffraction pattern with Cu—K α-rays of an α-type crystal of 1,1-bis(4-hydroxyphenyl)-1-phenylethane.

FIGS. 1 and 2 are patterns of X-ray diffraction states obtained through a powdery X-ray diffractometry and recorded through a high-speed semiconductor array detector, respectively. FIG. 1 is a β-type crystal of 1,1-bis(4-hydroxyphenyl)-1-phenylethane and shows one sharp and strong peak at 16.4°, three sharp peaks of intermediate intensity at each of 13°-16° and 17°-20.8° and at least three peaks of intermediate intensity at 22°-23° as to the diffraction angle (2θ). Moreover, in the diffraction angle of 1,1-bis(4-hydroxyphenyl)-1-phenylethane according to the invention, an error of about ±0.2° is allowable.

In the specification, the term "one sharp and strong peak" means a peak indicating a strongest intensity in the X-ray diffraction pattern. Further, the peak of "intermediate intensity" means a peak having an intensity of intermediate degree to the intensity of "one sharp and strong peak", concretely a peak having an intensity of approximately 30-70% to the intensity of the "one sharp and strong peak".

FIG. 2 is an α-type crystal of 1,1-bis(4-hydroxyphenyl)-1-phenylethane and shows an isolated strongish peak at 10°, a forked strong peak at 17°-17.5° and relatively strong peaks at 19°-23° as to the diffraction angle (2θ). (In the diffraction angle, an error of about ±0.2° is allowable.) FIGS. 1 and 2 clearly show the difference between both the crystals.

Although whether or not the α-type crystal of 1,1-bis(4-hydroxyphenyl)-1-phenylethane is converted into the β-type crystal according to the invention through the above treatment is judged by measuring the X-ray diffraction pattern, it is also judged by measuring a melting point of a sample (use of capillary) as a simpler judgment. As to mp (melting point) of each crystal form, the α-type crystal roughly has mp=185-190° C., while the β-type crystal becomes wider toward a lower temperature side and roughly has mp=170-190° C.

In the invention, the measuring device and measuring conditions are not particularly limited as long as the measurement is based on the X-ray diffractometry with Cu—K α-rays. The measuring device and conditions for powdery X-ray diffractometry in FIGS. 1 and 2 are as follows.

Measuring device: X'Pert-PRO-MPD (made by Spectris Co., Ltd.)
Target: Cu
Scanning angle: 5°~40.0°
Scanning rate: 0.2°/min
Tube voltage: 45 kV
Tube current: 40 mA
Incident slit: 0.04° solar slit, automated variable divergence slit, ASI
Light-receiving slit: 0.04° solar slit The heat-sensitive recording material according to the invention comprises a substrate and a heat-sensitive color-forming layer formed thereon, which contains a typically achromic to hypochromic color-forming compound and a color-developing compound capable of coloring the color-forming compound under heating, characterized in that the β-type crystal of 1,1-bis(4-hydroxyphenyl)-1-phenylethane according to the invention is included as the color-developing compound. Also, the heat-sensitive recording material according to the invention can be obtained by mixing the above color-forming compound and the β-type crystal of 1,1-bis(4-hydroxyphenyl)-1-phenylethane according to the invention and, if necessary, the other additives such as a binding agent, a filler, a sensitizer (heat-fusible compound) and the like and applying onto a substrate such as paper, plastic film, synthetic paper or the like as a heat-sensitive color-forming layer.

In the formation of the heat-sensitive color-forming layer according to the invention, the color-forming compound is used in an amount of usually 1-50% by mass, preferably 5-30% by mass in the heat-sensitive color-forming layer, and the β-type crystal of 1,1-bis(4-hydroxyphenyl)-1-phenylethane according to the invention is used in an amount of usually 1-70% by mass, preferably 10-50% by mass in the heat-sensitive color-forming layer, and the binding agent is used in an amount of usually 1-90% by mass in the heat-sensitive color-forming layer, and the filler and sensitizer (heat-fusible compound) are used in each amount of usually 0-80% by mass in the heat-sensitive color-forming layer, and other additives such as a lubricant, a surfactant, a defoaming agent, an ultraviolet ray absorber and the like are used in an arbitrary amount, for example, 0-30% by mass in the heat-sensitive color-forming layer, respectively. In a further preferable embodiment, as an amount of each component used among the above composition, the β-type crystal of 1,1-bis(4-hydroxyphenyl)-1-phenylethane is used within a range of usually 0.5-20 times, preferably 1-5 times to the color-forming compound at a mass ratio.

The color-forming compound used in the invention may be ones typically used in a pressure-sensitive recording paper or a heat-sensitive recording paper and is not particularly limited. As an example of the color-forming compound used are mentioned, for example, a fluoran-based compound, a triarylmethane-based compound, a spiro-based compound, a diphenylmethane-based compound, a thiazine-based compound, a lactam-based compound, a fluorene-based compound and the like. Moreover, these color-forming compounds may be used alone or in a combination of two or more.

As a concrete example of the usable fluoran-based compound are mentioned 3-diethylamino-6-methyl-7-anilinofluoran, 3-dibutylamino-6-methyl-7-anilinofluoran, 3-(N-methyl-N-cyclohexyl amino)-6-methyl-7-anilinofluoran, 3-(N-ethyl-N-isopentylamino)-6-methyl-7-anilinofluoran, 3-(N-ethyl-N -isobutylamino)-6-methyl-7-anilinofluoran, 3-[N- ethyl-N-(3-ethoxypropyl)amino]-6-methyl-7-anilinofluoran, 3-(N-ethyl-N-hexylamino)-6-methyl-7-anilinofluoran, 3-dipentylamino-6-methyl-7-anilinofluoran, 3-(N-methyl-N-propylamino)-6-methyl-7-anilinofluoran, 3-(N-ethyl-N-tetrahydrofurylamino)-6-methyl-7-anilinofluoran, 3-diethylamino-6-methyl-7-(p-chloroanilino)fluoran, 3-diethylamino-6-methyl-7-(p-fluoroanilino)fluoran, 3-[N-ethyl-N-(p-tolyl)amino]-6-methyl-7-anilinofluoran, 3-diethylamino-6-methyl-7-(p-toluidino)fluoran, 3-diethylamino-7-(o-chloroanilino)fluoran, 3-dibutylamino-7-(o-chloroanilino)fluoran, 3-diethylamino-7-(o-fluoroanilino)fluoran, 3-dibutylamino-7-(o-fluoroanilino)fluoran, 3-diethylamino-7-(3,4-dichloroanilino)fluoran, 3-pyrrolidino-6-methyl-7-anilinofluoran, 3-diethylamino-6-chloro-7-ethoxyethylaminofluoran, 3-diethylamino-6-chloro-7-anilinofluoran, 3-diethylamino-7-chlorofluoran, 3-diethylamino-7-methylfluoran, 3-diethylamino-7-octylfluoran, 3-{N-ethyl-N-(p-tolyl)amino}-6-methyl-7-phenetylfluoran and the like.

As a concrete example of the usable triarylmethan-based compound are mentioned 3,3-bis(p-dimethylaminophenyl)-6-dimethylaminophthalide (alias name: crystal violet lactone or CVL), 3,3-bis(p-dimethylaminophenyl)phthalide, 3-(p-dimethylaminophenyl)-3-(1,2-dimethylaminoindol-3-yl)phthalide, 3-(p-dimethylaminophenyl)-3-(2-methylindiol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-(2-phenylindol-3-yl)-5-dimethylaminophthalide, 3-p-dimethylaminophenyl-3-(1-methylpyrrol-2-yl)-6-dimethylaminophthalide and the like.

As a concrete example of the usable spiro-based compound are mentioned 3-methylspirodinaphthopyran, 3-ethylspirodinaphthopyran, 3,3'-dichlorospirodinaphthopyran, 3-benzylspirodinaphthopyran, 3-propylspirobenzopyran, 3-methylnaphtho-(3-methoxybenzo)spiropyran, 1,3,3-trimethyl-6-nitro-8'-methoxyspiro(indolyn-2,2'-benzopyran) and the like. As a concrete example of the usable diphenylmethane-based compound are mentioned N-halophenyl-leucoauramine, 4,4-bis-dimethylaminophenylbenzhydrylbenzyl ether, N-2,4,5-trichlorophenylleucoauramine and the like. As a concrete example of the thiazine-based compound are mentioned benzoylleucomethylene blue, p-nitrobenzoylleucomethylene blue and the like. As a concrete example of the lactam-based compound are mentioned Rhodamine B anilinolactam, Rhodamine B-p-chloroanilinolactam and the like. As a concrete example of the fluorene-based compound are mentioned 3,6-bis(dimethylamino)fluorenespiro(9,3')-6'-dimethylaminophthalide, 3,6-bis(dimethylamino)fluorenespiro(9,3')-6'-pyrrolidinophthalide, 3-dimethylamino-6-diethylaminofluorenespiro(9,3')-6'-pyrrolidinophthalide and the like. These color-forming compounds are used alone or in a mixture.

In the heat-sensitive recording material according to the invention, another color-developing compound may be further included in addition to the β-type crystal of 1,1-bis(4-hydroxyphenyl)-1-phenylethane. As the color-developing compound capable of being used together with the β-type crystal of 1,1-bis(4-hydroxyphenyl)-1-phenylethane may be used anyone typically used in the pressure-sensitive recording paper or heat-sensitive recording paper, which are not particularly limited. As a concrete example of the co-usable color-developing compound are mentioned phenolic compounds such as α-naphthol, β-naphthol, p-octylphenol, 4-t-octylphenol, p-t-butylphenol, p-phenylphenol, 1,1-bis(p-hydroxyphenyl)propane, 2,2-bis(p-hyroxyphenyl)propane (alias name: bisphenol A or BPA), 2,2-bis(p-hydroxyphenyl)butane, 1,1-bis(p-hydroxyphenyl)cyclohexane, 2,2-bis(3-methyl-4-hydroxyphenyl)propane, 2,2-bis(3-phenyl-4-hydroxyphenyl)propane, 4,4'-thiobisphenol, 4,4'-cyclo-hexylidenediphenol, 2,2'-bis(2,5-dibromo-4-hydroxyphenyl)propane, 4,4'-isopropylidenebis(2-t-butylphenol), 2,2'-methylenebis(4-chlorophenol), 4,4'-dihydroxydiphenylsulfon, 2,4'-dihydroxydiphenylsulfon, bis(3-allyl-4-hydroxyphenyl)sulfon, 4-hydroxy-4'-allyloxydiphenylsulfon, 4-hydroxy-4'-benzyloxydiphenylsulfon, 4-hydroxy-4'-isopropoxydiphenylsulfon, methyl bis(4-hydroxyphenyl) acetate, butyl bis(4-hydroxyphenyl)acetate, benzyl bis(4-hydroxyphenyl)acetate and the like; aromatic carboxylic acid derivatives, aromatic carboxylic acids or polyvalent metal salts thereof such as benzyl p-hydroxybenzoate, ethyl p-hydroxybenzoate, dibenzyl 4-hydroxyphthalate, dimethyl 4-hydroxyphthalate, ethyl 5-hydroxyisophthalate, 3,5-di-t-butylsalicylic acid and the like. However, it is not limited thereto.

The amount of the color-developing compound co-usable with the β-type crystal of 1,1-bis(4-hydroxyphenyl)-1-phenylethane is preferable to be within a range not obstructing the effect of the invention, for example, an amount not exceeding the content of the β-type crystal of 1,1-bis(4-hydroxyphenyl)-1-phenylethane.

As the sensitizer (heat-fusible compound) used in the heat-sensitive recording material according to the invention may be waxes such as animal and plant waxes, synthetic wax and the like; and ones being solid at room temperature, preferably having a melting point of not lower than about 70° C. such as higher fatty acids, higher fatty acid amides, higher fatty acid anilides, naphthalene derivatives, aromatic ethers, aromatic carboxylic acid derivatives, aromatic sulfonic acid esters, carbonic or oxalic acid diesters, biphenyl derivatives, terphenyl derivatives, sulfon derivatives and the like.

As the wax are mentioned Japan wax, carnauba wax, shellac, paraffin, montan wax, oxidized paraffin, polyethylene wax, oxidized polyethylene and the like. As the higher fatty acid are mentioned stearic acid, behenic acid and the like. As the higher fatty acid amide are mentioned stearic acid amide, oleic acid amide, N-methylstearic acid amide, erucic acid amide, methylol behenic acid amide, methylenebisstearic acid amide, ethylenebisstearic acid amide and the like. As the higher fatty acid anilide are mentioned stearic acid anilide, linoleic acid anilide and the like. As the naphthalene derivative are mentioned 1-benzyloxynaphthalene, 2-benzyloxynaphthalene, 1-hydroxynaphthoic acid phenyl ester and the like. As the aromatic ether are mentioned 1,2-diphenoxyethane, 1,4-diphenoxyethane, 1,2-bis(3-methylphenoxy)ethane, 1,2-bis(4-methoxyphenoxy)ethane, 1,2-bis(3,4-dimethylphenyl)ethane, 1-phenoxy-2-(4-chlorophenoxy)ethane, 1-phenoxy-2-(4-methoxyphenoxy)ethane, 1,2-diphenoxymethylbenzene and the like. As the aromatic carboxylic acid derivative are mentioned p-hydroxybenzoic acid benzylester, p-benzyloxybenzoic acid benzyletser, terephthalic acid dibenyletser and the like. As the aromatic sulfonic acid ester are mentioned p-toluenesulfonic acid phenylester, pehnylmesitylene sulfonate, 4-methylphenylmesitylene sulfonate and the like. As the carbonic or oxalic acid diester are mentioned diphenyl carbonate, dibenzyl oxalate, di(4-chlorobenzyl) oxalate, di(4-methylbenzyl) oxalate and the like. As the biphenyl derivative are mentioned p-benzylbiphenyl, p-acetylbiphenyl, p-allyloxybiphenyl and the like. As the terphenyl derivative are mentioned m-terphenyl and the like. As the sulfon derivative are mentioned diphenylsulfon and the like. They may be used alone or in a combination of two or more. Among them are particularly preferable stearic acid amide, 2-benzyloxynaphthalene, 1,2-diphenoxyethane, 1,2-bis(3-methylphenoxy)ethane, 1,2-diphenoxymethylbenzene, di(4-chlorobenzyl)oxalate, di(4-methylbenzyl)oxalate, p-benzylbiphenyl, p-acetylbiphenyl, diphenylsulfon and the like. The latter compounds may be used alone or in a combination of two or more.

As a concrete example of the usable binding agent are mentioned water-soluble compounds such as methylcellulose, methoxycellulose, hydroxyethylcellulose, carboxymethylcellulose, sodium carboxymethylcellulose, cellulose, polyvinyl alcohol (PVA), carboxyl group-modified polyvinyl alcohol, sulfonic acid group-modified polyvinyl alcohol, polyvinyl pyrrolidone, polyacrylamide, polyacrylic acid, starch and its derivatives, casein, gelatin, water-soluble isoprene rubber, an alkali salt of styrene-maleic anhydride copolymer, an alkali salt of iso(or diiso)butylene/maleic anhydride copolymer and the like; or a hydrophobic polymer emulsion of styrene/butadiene (BS) copolymer, carboxylated styrene/butadiene (CSB) copolymer, styrene/butadiene/acrylic acid-based copolymer, polyvinyl acetate, polyvinyl chloride, vinyl chloride/vinyl acetate copolymer, polystyrene, acrylic resin, acryl/styrene resin, polyacrylic acid ester, polybutyral, epoxy resin, furan resin, vinyltoluene resin, rosin ester resin, composite particles of colloidal silica and acryl copolymer; and so on.

As a concrete example of the usable filler are mentioned calcium carbonate, magnesium carbonate, magnesium oxide, silica, white carbon, talc, clay, alumina, magnesium hydroxide, aluminum hydroxide, aluminum oxide, barium sulfate, polystyrene resin, urea-formalin resin and the like.

Furthermore, various additives other than the above ones may be used in the heat-sensitive recording material according to the invention. As an example of the usable additive are mentioned, for example, a metal salt of a higher fatty acid such as zinc stearate, calcium stearate or the like for the purpose of prevention of thermal head wearing, sticking prevention or the like, a phenol derivative for giving an oxidation resistance or an anti-aging effect, a ultraviolet ray absorber such as a benzophenone-based compound, a benzotriazole-based compound or the like, various surfactants, defoaming agents and so on.

The heat-sensitive recording material according to the invention is prepared by using the above materials, for example, according to the following method. That is, each of the color-forming compound and the β-type crystal of 1,1-bis(4-hydroxyphenyl)-1-phenylethane is first pulverized and dispersed in a dispersing machine such as ball mill, attritor, sand mill or the like, if necessary, together with a binding agent, a sensitizer (heat-fusible compound) and other additives (water is usually used as a medium in wet-type pulverization-dispersion) and then mixed to prepare a coating solution for a heat-sensitive color-forming layer, and the coating solution is applied onto a substrate such as paper (high-quality paper, plain paper, coat paper or the like may be used), plastic sheet, synthetic paper or the like, with a bar coater, a blade coater or the like so as to be usually 1-20 g/m² as a dry weight and then dried to obtain the heat-sensitive recording material according to the invention.

Also, a middle layer well-known itself may be disposed between the heat-sensitive color-forming layer and the substrate, or an overcoat layer (protection layer) may be disposed on the heat-sensitive color-forming layer, if necessary.

The heat-sensitive recording material according to the invention formed by disposing the heat-sensitive color-forming layer containing the typically achromic to hypochromic color-forming compound and the β-type crystal of 1,1-bis(4-hydroxyphenyl)-1-phenylethane On the substrate is excellent in the storing stability of a colored image and a non-coloring portion against heat, water and the like and excellent in the recording properties such as a low-energy color development capable of coloring at a high speed and the like.

EXAMPLES

The following examples are given in illustration of the invention and are not intended as limitations thereof. In the representation of the composition for the examples, "part" means part by mass and "%" means % by mass, respectively. In the examples, the measurement of a melting point is carried out by using a capillary method. Moreover, the measuring device and conditions used in powdery X-ray diffractometry for confirming crystal form are as follows.

Measuring device: X'Pert-PRO-MPD (made by Spectris Co., Ltd.)
Target: Cu
Scanning angle: 5°~40.0°
Scanning rate: 0.2°/min
Tube voltage: 45 kV
Tube current: 40 mA
Incident slit: 0.04° solar slit, automated variable divergence slit, ASI
Light-receiving slit: 0.04° solar slit <Preparation of β-type crystal of 1,1-bis(4-hydroxyphenyl)-1-phenylethane>

Example 1

As 1,1-bis(4-hydroxyphenyl)-1-phenylethane known as a trade name: BisP-AP made by Honshu Chemical Industry Co., Ltd. is examined by powdery X-ray diffractometry using the above device and conditions, it shows an X-ray diffraction pattern as shown in FIG. 2 and is confirmed to be an α-type crystal. As the melting-point is further measured, it is mp=185-186° C.

100 parts of the α-type crystal of 1,1-bis(4-hydroxyphenyl)-1-phenylethane is dissolved in 100 parts of ethanol at 60° C. and 300 parts of water is added to conduct crystallization with stirring. Then, the resulting precipitated crystals are filtered, washed with water and dried to obtain 98 parts of crystal. The thus obtained crystal shows an X-ray diffraction pattern as shown in FIG. 1 in the same X-ray diffractometry and is confirmed to be a β-type crystal of 1,1-bis(4-hydroxyphenyl)-1-phenylethane through conversion from α type to β type crystal form. As the melting point is further measured, it is mp=172-186° C.

Comparative Example 1

The trade name: BisP-AP made by Honshu Chemical Industry Co., Ltd. and used in Example 1 is recrystallized according to a method described in Example 13 of Table 1 in Chinese Patent Application No. CN1557797 as follows.

Into 250 g of a mixed solvent of toluene/ethanol at a volume ratio of 100/3 is added BisP-AP (50 g), which is refluxed under heating. The temperature in the reaction system during the reflux is 94-94.5° C. After 10 minutes from the start of the reflux, the heating is stopped and the cooling is conducted in an ice water. After 1 hour, the precipitated crystal is filtered and washed with the toluene-ethanol mixed solvent of the same volume ratio. The resulting crystal is dried at 70° C. over a night to obtain a crystal. As a result of the powdery X-ray diffractometry the resulting crystal shows an X-ray diffraction pattern as shown in FIG. 2 and is confirmed to be the same α-type crystal as in the BisP-AP as a starting material and also confirmed to cause no conversion of crystal form. As the melting point of the crystal is further measured, it is mp=182-188° C.

Comparative Example 2

According to a method described in Example 3 of JP-A-S62-178534 are reacted 84.7 g of phenol, 36 g of acetophenone and 1 ml of mercaptoacetic acid by raising a temperature to 60° C. and stirring while blowing a hydrogen chloride gas for 10 hours. The resulting purified crystal is washed with warm water 3 times to obtain 55 g of a crude product of 1,1-bis(4-hydroxyphenyl)-1-phenylethane (purity: 76.7%, document value: 92.8%). The thus obtained crude product is further purified by using a mixed solvent of 120 ml of methanol and 60 ml of xylene described in Example 3 of the same document. The resulting crystal (purity: 90.7%) shows an X-ray diffraction pattern as shown in FIG. 2 through the same powdery X-ray diffractometry as in Example 1 and is confirmed to be an α-type crystal. As the melting point is further measured, it is mp=182-185°C.

Comparative Example 3

The same procedure as in Comparative Example 2 is repeated except that a mixed solvent of 120 ml of isopropanol and 60 ml of toluene is used instead of the mixed solvent of 120 ml of methanol and 60 ml of xylene used in the purification of Comparative Example 2 to conduct the purification of the crude product. The resulting crystal (purity: 95.1 %) shows an X-ray diffraction pattern as shown in FIG. 2 through the same powdery X-ray diffractometry as in Example 1 and is confirmed to be an α-type crystal. As the melting point is further measured, it is mp=183-185° C.

Comparative Example 4

Figure 3:
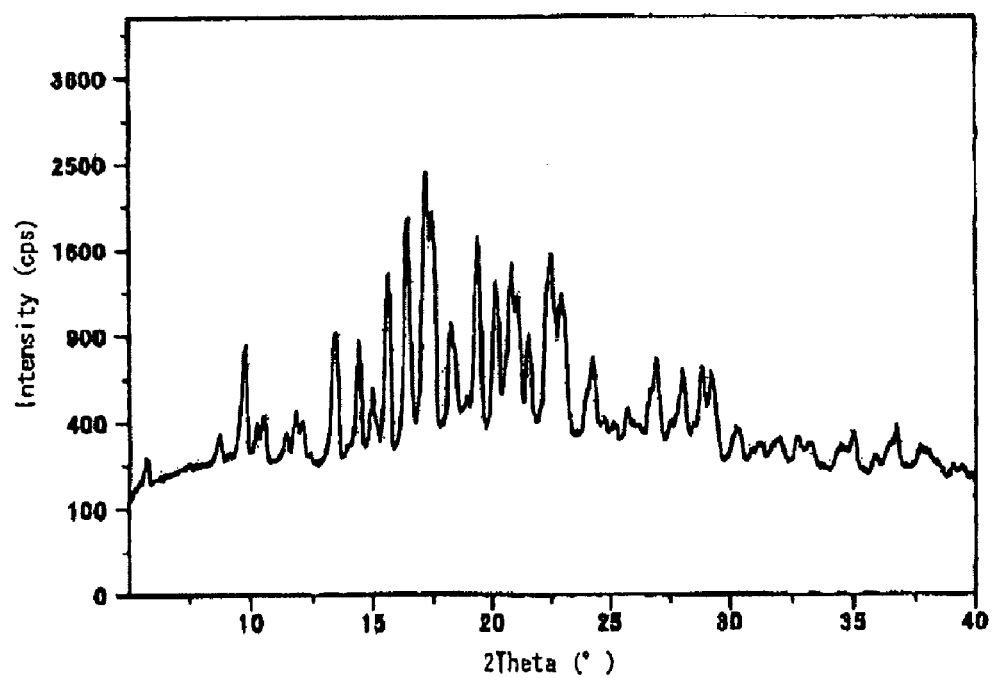
FIG. 3 is an X-ray diffraction pattern with Cu—K α-rays of a mixture of α-type crystal and β-type crystal of 1,1-bis(4-hydroxyphenyl)-1-phenylethane.

The same procedure as in Comparative Example 2 is repeated except that a mixed solvent of 120 ml of methanol and 60 ml of toluene is used instead of the mixed solvent of 120 ml of methanol and 60 ml of xylene used in the purification of Comparative Example 2 to conduct the purification of the crude product. The resulting crystal (purity: 99.0%) is confirmed to have an X-ray diffraction pattern as shown in FIG. 3 through the same powdery X-ray diffractometry as in Example 1. As the melting point is further measured, it is mp=185-188° C. As being classified from the melting point, the resulting crystal is an α-type crystal, while the powdery X-ray diffractometry provides the X-ray diffraction pattern as shown in FIG. 3. In FIG. 3 are shown an isolated strongish peak at 10° and relatively strong peaks at 19°-23°, which have clearly a characteristic of the α-type crystal, but a sharp and strong peak is shown at 16.4° inherent to a β-type crystal, from which it is considered to obtain a mixture of the α-type and β-type crystals.

<Preparation of Heat-sensitive Recording Material>

Example 2

(Formation of Heat-sensitive Color-forming Layer)

A mixture having the following composition is pulverized and dispersed so as to have an average particle size of not more than 1 μm with a sand grinder, whereby [A] solution and [8] solution are prepared, respectively.

[A] solution:

| 3-dibutylamino-6-methyl-7-anilinofluoran | 25 parts |
| Aqueous solution of 25% PVA*1 | 20 parts |
| Water | 55 parts |

[B]solution:

| 1,1-bis(4-hydroxyphenyl)-1-phenylethane of β-type crystal obtained in Example 1 | 25 parts |
| Aqueous solution of 25% PVA*1 | 20 parts |
| Water | 55 parts |

Then, each of the above solutions and the following chemicals are mixed at the following ratio to prepare a coating solution for a heat-sensitive color-forming layer, which is applied onto a high-quality paper having a basis weight of 50 g/m² so as to render into a dry weight of 8 g/m² and dried to form a heat-sensitive color-forming layer.

| [A] solution | 8 parts |
| [B] solution | 20 parts |
| Aqueous dispersion of 50% calcium carbonate | 10 parts |
| Emulsion of 48% carboxylated SB copolymer*2 | 6 parts |

*1 made by Nippon Synthetic Chemical Industry Co., Ltd. GOHSENOL GL-05R, polymerization degree of not more than 1000, saponification degree of 86.5-89.0 mol %, 25 g of PVA is dissolved in 75 g of water under heating in use
*2 made by Asahi Kasei Corporation, ASAHIKASEI latex L7063, use of about 48% modified styrene-butadiene copolymer latex (Formation of Protection Layer)

Then, a mixture having the following composition is prepared to form a coating solution for a protection layer, which is applied onto the above heat-sensitive color-forming layer so as to render into a dry weight of 3 g/m² and dried to obtain a heat-sensitive recording material provided with a protection layer according to the invention.

| Emulsion of 40% styrene/acrylic ester copolymer *3 | 17 parts |
| Aqueous dispersion of 5% bentonite *4 | 30 parts |
| Aqueous dispersion of 30% zinc stearate | 8 parts |

*3 made by Saiden Chemical Industry Co., Ltd. SAIBINOL EK-41, an aqueous emulsion of 45% styrene/acryl copolymer is diluted with water up to a concentration of 40% in use
*4 made by Kunimine Industires Co., Ltd. KUNIPIA G, 5 g of colloidal water-containing aluminum silicate is dissolved in 95 g of water in use Example 3

A heat-sensitive recording material proved with a protection layer according to the invention is obtained in the same manner as in Example 2 except that 3-dipentylamino-6-ethyl-7-anilinofluoran is used instead of 3-dibutylamino -6-methyl-7-anilinofluoran in the [A] solution of Example 2.

Example 4

A heat-sensitive recording material proved with a protection layer according to the invention is obtained in the same manner as in Example 2 except that 3-(N-ethyl-N-isopentylamino)-6-methyl-7-anilinofluoran is used instead of 3-dibutylamino-6-methyl-7-anilinofluoran in the [A] solution of Example 2.

Comparative Example 5

A heat-sensitive recording material for comparison is obtained in the same manner as in Example 2 except that an α-type crystal of 1,1-bis(4-hydroxyphenyl)-1-phenylethane, i.e. a trade name: BisP-AP made by Honshu Chemical Industry Co., Ltd. is used without transforming the crystal form instead of the β-type crystal of 1,1-bis(4-hydroxyphenyl)-1-phenylethane in the [B] solution of Example 2. Moreover, the purity of BisP-AP used is 99.88% (area %) as measured by RPLC (high-speed liquid chromatography).

Comparative Example 6

A heat-sensitive recording material for comparison is obtained in the same manner as in Example 2 except that bisphenol A is used instead of the β-type crystal of 1,1-bis(4-hydroxyphenyl)-1-phenylethane in the [B] solution of Example 2.

Comparative Example 7

A heat-sensitive recording material for comparison is obtained in the same manner as in Example 2 except that the α-type crystal obtained in Comparative Example 1 is used instead of the β-type crystal of 1,1-bis(4-hydroxyphenyl)-1-phenylethane in the [B] solution of Example 2.

Comparative Examples 8-10

A heat-sensitive recording material for Comparative Example 8 is obtained in the same manner as in Example 2 except that the crystal obtained in Comparative Example 2 is used instead of the β-type crystal of 1,1-bis(4-hydroxyphenyl)-1-phenylethane in the [B] solution of Example 2. Similarly, a heat-sensitive recording material for Comparative Example 9 is obtained by using the crystal obtained in Comparative Example 3, and a heat-sensitive recording material for Comparative Example 10 is obtained by using the crystal obtained in Comparative Example 4.

The following test for quality performance is carried out with respect to the thus obtained invention and comparative heat-sensitive recording materials, respectively.

TABLE 1

Test for quality performance

|  | Quality performance | | | |
| --- | --- | --- | --- | --- |
|  | matrix 1) | low-temperature color formation 2) | high-temperature color formation 3) | heat resistance 4) |
| Example 2 | 0.06 | 1.35 | 1.39 | 0.06/1.25 |
| Example 3 | 0.06 | 1.35 | 1.40 | 0.06/1.25 |
| Example 4 | 0.05 | 1.38 | 1.46 | 0.07/1.43 |
| Comparative Example 5 | 0.06 | 0.56 | 1.10 | 0.06/0.99 |
| Comparative Example 6 | 0.05 | 1.36 | 1.36 | 0.10/1.44 |
| Comparative Example 8 | 0.06 | 0.58 | 1.12 | 0.06/0.98 |
| Comparative Example 9 | 0.06 | 0.57 | 1.11 | 0.06/0.98 |
| Comparative Example 10 | 0.06 | 0.59 | 1.19 | 0.06/1.04 |

TABLE 2

(continued from Table 1)

|  | Quality performance | |
| --- | --- | --- |
|  | humidity resistance 5) | water resistance 6) |
| Example 2 | 0.06/1.25 | 1.00 |
| Example 3 | 0.06/1.26 | 1.01 |
| Example 4 | 0.07/1.39 | 1.10 |
| Comparative Example 5 | 0.06/0.90 | 0.75 |
| Comparative Example 6 | 0.11/1.28 | 0.64 |
| Comparative Example 8 | 0.06/0.88 | 0.78 |
| Comparative Example 9 | 0.06/0.90 | 0.75 |
| Comparative Example 10 | 0.06/0.95 | 0.77 |

1) matrix: value of a non-colored portion of a sample measured by Macbeth reflection densitometer (RD-914 Model, made by Macbeth) (Macbeth reflection density)
2) low-temperature color formation: Macbeth reflection density of an image portion of a sample colored under conditions of printing pressure: 0.098 MPa, 120° C. and 1 second with a thermal slope testing machine (HG-100, made by Toyo Seiki Co., Ltd.)
3) high-temperature color formation: Macbeth reflection density of an image portion of a sample colored under conditions of printing pressure: 0.098 MPa, 150° C. and 1 second with a thermal slope testing machine (HG-100, made by Toyo Seiki Co., Ltd.)
4) heat resistance: Macbeth reflection densities of non-colored portion and image portion after the sample colored in the item 3) is left to stand in a constant temperature vessel of 60° C. for 24 hours (non-colored portion/image portion)
5) humidity resistance: Macbeth reflection densities of non-colored portion and image portion after the sample colored in the item 3) is left to stand in a constant humidity vessel having a relative humidity of 90% at 40° C. and for 24 hours (non-colored portion/image portion)
6) water resistance: Macbeth reflection density of an image portion after the sample colored in the item 3) is immersed in tap water of 25° C. for 24 hours As seen from Tables 1 and 2, the Macbeth reflection density of the image portion at 2) low-temperature color formation is 1.35-1.38 in Examples 2-4 and 0.56 in Comparative Example 5, from which it is revealed that the heat-sensitive recording material using the β-type crystal of 1,1-bis(4-hydroxyphenyl)-1-phenylethane according to the invention is excellent in the low-temperature color-developing property as compared with the heat-sensitive recording material of Comparative Example 5 using the α-type crystal.

Also, the density in 3) high-temperature color development is 1.39-1.46 in Examples 2-4 and 1.10 in Comparative Example 5, which means that the heat-sensitive recording material of Comparative Example 5 is still insufficient in the color forming property.

In the tests of 4) heat resistance, 5) humidity resistance and 6) water resistance, the densities are 1.25-1.43 (image portion), 1.25-1.39 (image portion) and 1.00-1.10 in Examples 2-4, respectively, while the densities are 0.99 (image portion), 0.90 (image portion) and 0.75 in Comparative Example 5, respectively, from which it is clear that the heat-sensitive recording material of Comparative Example 5 clearly observes a color degradation of the image and has a serious problem in the image stability.

In Comparative Example 6 using bisphenol A as a color-developing compound, the Macbeth reflection densities of the non-colored portion in 4) heat resistance and 5) humidity resistance are 0.10 and 0.11, respectively, while those in Examples 2-4 are 0.06-0.07 and 0.06-0.07, respectively, so that the fogging tendency is recognized in the heat-sensitive recording material of Comparative Example 6.

Further, the density in 6) water resistance is 1.00-1.10 in Examples 2-4 and 0.64 in Comparative Example 6, from which it is clear that the heat-sensitive recording material of Comparative Example 6 has a problem in the water resistance of the image.

As seen from Comparative Examples 8 and 9, in order to obtain the β-type crystal according to the invention, it is required to use ethanol as an alcohol being a solvent capable of dissolving the crystal. If an alcohol such as methanol, isopropanol or the like is used, as seen from Comparative Example 10, the mixture of α-type crystal and β-type crystal may be obtained, but only the β-type crystal according to the invention can not be obtained alone. Furthermore, it is important that water is used as an insoluble solvent for the crystal and the crystallization is conducted from a solvent system of ethanol/water. The β-type crystal according to the invention is also excellent in the performance as a color-developing agent as compared with the α-type crystal or the mixture of α-type crystal and β-type crystal, and particularly has a significant characteristic that the fogging of the matrix (color change of non-colored portion) is not caused in addition to the excellent low-temperature color-forming property applicable for high-speed color formation. Therefore, the heat-sensitive recording material using the β-type crystal according to the invention as a color-developing agent is clearly beneficial.

Next, the tests for quality performance on 1) matrix and 3) high-temperature color formation are conducted in the same manner as previously mentioned with respect to the heat-sensitive recording materials of Example 2 and Comparative Examples 5 and 7, respectively. The results are shown in is Table 3. Moreover, the reason why the content of Table 3 is different from the content of Table 1 in Example 2 and Comparative Example 5 is due to the fact that even if the heat-sensitive recording materials are prepared under the same conditions, when the preparation date are different, the completely same numerical values are not necessarily obtained and the error in the measurement is caused.

TABLE 3

Test for quality performance

| | Quality performance | |
|---|---|---|
| | matrix 1) | high-temperature color formation 3) |
| Example 2 | 0.05 | 1.50 |
| Comparative Example 5 | 0.05 | 1.14 |
| Comparative Example 7 | 0.05 | 1.16 |

As seen from Table 3, it is confirmed that there is no difference in the matrix 1) and the fogging is not caused in any cases. However, Comparative Example 5 using the α-type crystal and Comparative Example 7 using the α-type crystal obtained in Comparative Example 1 are 1.14 and 1.16 in the high-temperature color formation 3), respectively, which are confirmed that the coloring density is low and the color-forming property is insufficient as compared with Example 2 of 1.50 using the β-type crystal.

The invention claimed is:

1. An isolated β-type crystal of 1,1-bis(4-hydroxyphenyl)-1-phenylethane, characterized by an X-ray diffraction pattern having one sharp and strong peak at 16.4° and three sharp peaks of intermediate intensity at each of 13°-16° and 17°-20.8° and at least three peaks of intermediate intensity at 22°-23° as a diffraction angle (2Θ) in an X-ray diffractometry with Cu—K α-rays.

2. A heat-sensitive recording material comprising a substrate and a heat-sensitive color-forming layer formed thereon, which contains a typically achromic to hypochromic color-forming compound and a color-developing compound capable of coloring the color-forming compound under heating, characterized in that isolated β-type crystal of 1,1-bis(4-hydroxyphenyl)-1-phenylethane is included as the color-developing compound and said β-type crystal of 1,1-bis(4-hydroxyphenyl)-1-phenylethane is characterized by an X-ray diffraction pattern having one sharp and strong peak at 16.4° and three sharp peaks of intermediate intensity at each of 13°-16° and 17°-20.8° and at least three peaks of intermediate intensity at 22°-23° as a diffraction angle (2θ) in an X-ray diffractometry with Cu—K α-rays.

3. A method for producing β-type crystal of 1,1-bis(4-hydroxyphenyl)-1-phenylethane comprising:
dissolving α-type crystal of 1,1-bis(4-hydroxyphenyl)-1-phenylethane in ethanol; and
adding water to conduct crystallization.

4. β-type crystal of 1,1-bis(4-hydroxyphenyl)-1-phenylethane produced by the method according to claim 3, wherein said β-type crystal of 1,1-bis(4-hydroxyphenyl)-1-phenylethane has a crystal form characterized by an X-ray diffraction pattern having one sharp and strong peak at 16.4° and three sharp peaks of intermediate intensity at each of 13°-16° and 17°-20.8° and at least three peaks of intermediate intensity at 22°-23° as a diffraction angle (2θ) in an X-ray diffractometry with Cu—K α-rays.

5. A heat-sensitive recording material comprising a substrate and a heat-sensitive color-forming layer formed thereon, which contains a typically achromic to hypochromic color-forming compound and a color-developing compound capable of coloring the color-forming compound under heating, characterized in that β-type crystal of 1,1-bis(4-hydroxyphenyl)-1-phenylethane is included as the color-developing compound, and said β-type crystal of 1,1-bis(4-hydroxyphenyl) 1-phenylethane is produced by the method according to claim 3 and has a crystal form characterized by an X-ray diffraction pattern having one sharp and strong peak at 16.4° and three sharp peaks of intermediate intensity at each of 13°-16° and 17°-20.8° and at least three peaks of intermediate intensity at 22°-23° as a diffraction angle (2θ) in an X-ray diffractometry with Cu—K α-rays.

* * * * *